US012624008B2

(12) United States Patent
Ramsden et al.

(10) Patent No.: US 12,624,008 B2
(45) Date of Patent: May 12, 2026

(54) 4-((6-OXOPYRIMIDIN-1(6H)-YL)METHYL) BENZOIC ACID AS AN INDUCER OF Z A1AT SECRETION FOR TREATING AATD

(71) Applicant: CENTESSA PHARMACEUTICALS (UK) LIMITED, Altrincham (GB)

(72) Inventors: Nigel Ramsden, Babraham (GB); David John Fox, Babraham (GB); James Andrew Huntington, Altrincham (GB)

(73) Assignee: CENTESSA PHARMACEUTICALS (UK) LIMITED, Altrincham (GB)

(*) Notice: Subject to any disclaimer, the term of this patent is extended or adjusted under 35 U.S.C. 154(b) by 0 days.

(21) Appl. No.: 18/081,793

(22) Filed: Dec. 15, 2022

(65) Prior Publication Data

US 2024/0327357 A1 Oct. 3, 2024

Related U.S. Application Data

(63) Continuation of application No. PCT/GB2021/051496, filed on Jun. 15, 2021.

(30) Foreign Application Priority Data

Jun. 15, 2020 (GB) ...................................... 2009074

(51) Int. Cl.
*C07D 239/36* (2006.01)
*A61K 31/513* (2006.01)

(52) U.S. Cl.
CPC .......... *C07D 239/36* (2013.01); *A61K 31/513* (2013.01)

(58) Field of Classification Search
None
See application file for complete search history.

(56) References Cited

U.S. PATENT DOCUMENTS

| | | | |
|---|---|---|---|
| 8,436,013 | B2 | 5/2013 | Liu et al. |
| 2007/0167621 | A1 | 7/2007 | Durley |
| 2016/0340319 | A1 | 11/2016 | Gnamm et al. |

FOREIGN PATENT DOCUMENTS

| | | | | |
|---|---|---|---|---|
| WO | WO-2019243841 A1 | 12/2019 | | |
| WO | WO-2020081257 A1 | 4/2020 | | |
| WO | WO-2020120992 A1 | 6/2020 | | |
| WO | WO-2021116706 A1 * | 6/2021 | .......... | C07D 403/10 |
| WO | WO-2021255436 A1 | 12/2021 | | |

OTHER PUBLICATIONS

Berthelier et al. Discovery of an Inhibitor of Z-Alpha1 Antitrypsin Polymerization. PLoS One 10(5):e0126256 (May 11, 2015).

(Continued)

*Primary Examiner* — Rachael E Bredefeld
(74) *Attorney, Agent, or Firm* — WILSON SONSINI GOODRICH & ROSATI

(57) ABSTRACT

The invention relates to 4-((6-oxopyrimidin-1(6H)-yl) methyl)benzoic acid, compositions thereof, and uses of either, for example in the treatment of $\alpha_1$-antitrypsin deficiency (A1AD or AATD).

4 Claims, 1 Drawing Sheet

(56) References Cited

OTHER PUBLICATIONS

Bouchecareilh et al. Histone deacetylase inhibitor (HDACi) suberoylanilide hydroxamic acid (SAHA)-mediated correction of a1-antitrypsin deficiency. J Biol Chem 287(45):38265-38278 (2012).
Burrows et al. Chemical chaperones mediate increased secretion of mutant alpha 1-antitrypsin (alpha 1-AT) Z: A potential pharmacological strategy for prevention of liver injury and emphysema in alpha 1-AT deficiency. PNAS USA 97(4):1796-1801 (2000).
CAS Registry Nos. 1797054-78-4 and 1219580-65-0 (Feb. 7, 2018).
Chang et al. Small-molecule peptides inhibit Z alpha1-antitrypsin polymerization. J. Cell. Mol. Med. 13(8B):2304-2316 (2009).
Elliott et al. Topography of a 2.0 A structure of alpha1-antitrypsin reveals targets for rational drug design to prevent conformational disease. Protein Science 9:1274-1281 (2000).
Huntington. How and why the Z variant of $\alpha_1$-antitrypson polymerises, and what can be done about it. $7^{th}$ International Symposium on Serpin Biology, Structure and Function. Powerpoint presention (Apr. 1, 2014).
Huntington. How and why the Z variant of $\alpha_1$-antitrypson polymerises, and what can be done about it. $XIII^{th}$ International Symposium on Proteinases, Inhibitors and biological Control. PowerPoint presentation (2012).
Knaupp et al. Kinetic instability of the serpin Z alpha1-antitrypsin promotes aggregation. J. Mol. Biol. 396:375-383 (2010).
Mallya et al. Small molecules block the polymerization of Z alpha1-antitrypsin and increase the clearance of intracellular aggregates. J Med Chem 50(22):5357-5363 (2007).
Parfrey et al. Targeting a surface cavity of alpha 1-antitrypsin to prevent conformational disease. J. Biol. Chem. 278(35):33060-33066 (2003).
PCT/GB2021/051496 International Search Report and Written Opinion dated Aug. 24, 2021.
GB2009074.2 Search Report dated Nov. 23, 2020.

* cited by examiner

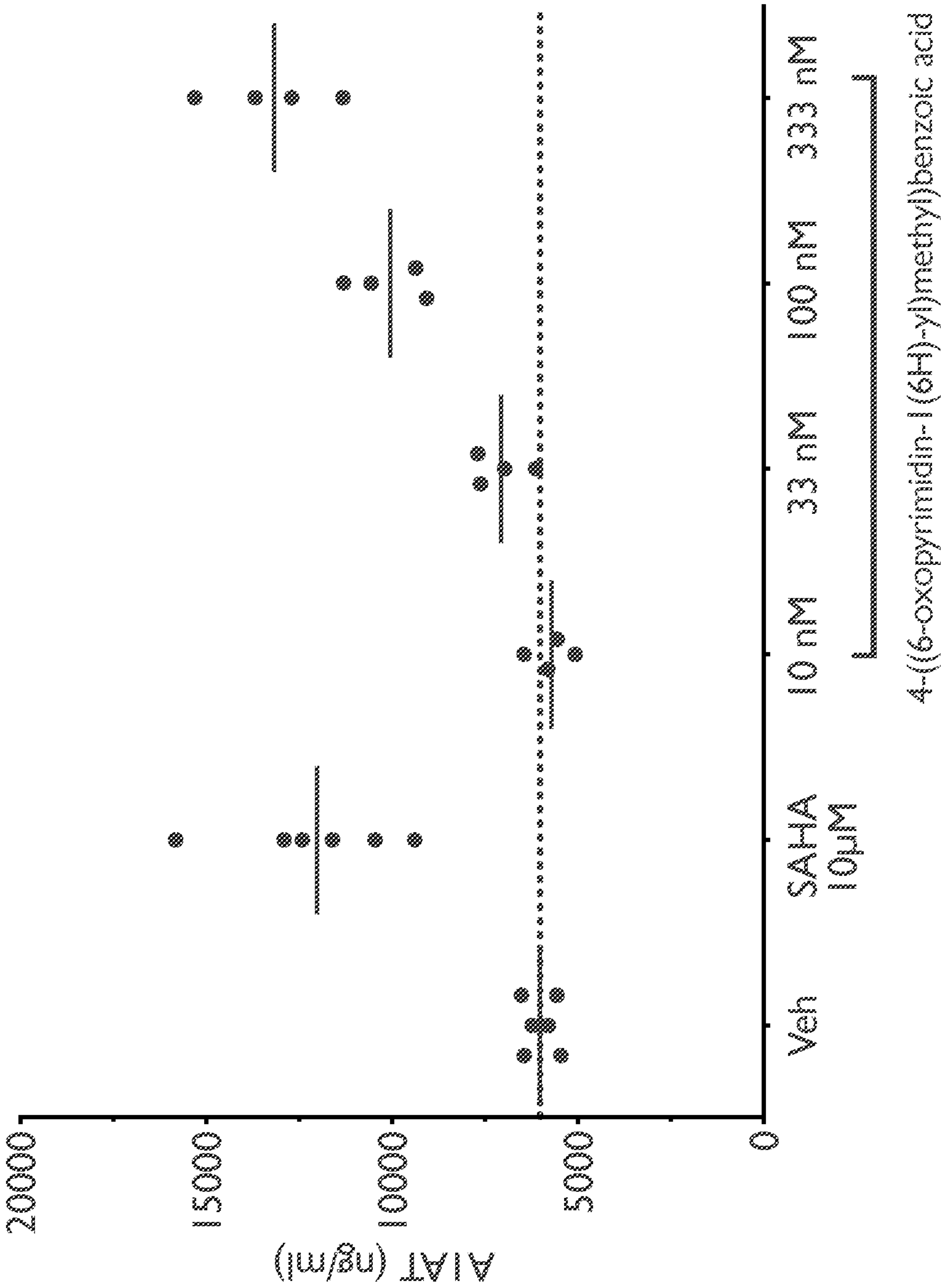
A1AT (ng/ml)
20000
15000
10000
5000
0
Veh
SAHA
10μM
10 nM
33 nM
100 nM
333 nM
4-((6-oxopyrimidin-1(6H)-yl)methyl)benzoic acid

4-((6-OXOPYRIMIDIN-1(6H)-YL)METHYL) BENZOIC ACID AS AN INDUCER OF Z A1AT SECRETION FOR TREATING AATD

CROSS REFERENCE

This application is a continuation of International Application No. PCT/GB2021/051496, filed Jun. 15, 2021, which is incorporated herein by reference in its entirety.

SUMMARY OF THE DISCLOSURE

The invention relates to a composition comprising 4-((6-oxopyrimidin-1(6H)-yl)methyl)benzoic acid, uses thereof and uses of 4-((6-oxopyrimidin-1(6H)-yl)methyl)benzoic acid.

$\alpha_1$-Antitrypsin (A1AT) is a member of the serpin superfamily produced by the liver and secreted into the blood. It inhibits a variety of serine proteases, especially neutrophil elastase. When blood levels of A1AT are low, excessive neutrophil elastase activity degrades lung tissue resulting in respiratory complications such as chronic obstructive pulmonary disease (COPD).

The reference range of A1AT in blood is 0.9-2.3 g/L. Levels lower than this are typical of $\alpha_1$-antitrypsin deficiency (A1AD or AATD), a genetic disorder caused by mutations in the SERPINA1 gene, coding for A1AT. The Z mutation, the most common cause of AATD, is the substitution of glutamate to lysine at position 366 of A1AT (UniProtKB-P01009 (A1AT_HUMAN)), corresponding to position 342 in the mature protein (Z A1AT). The Z mutation affects the folding of AAT resulting in only a small fraction acquiring the native/active state. The remainder is either cleared as misfolded protein or accumulates in the liver as stable polymers. As a consequence of the misfolding, homozygous carriers of the Z mutation (ZZ) have plasma levels of A1AT that are 10-15% of normal, predisposing carriers to COPD. Accumulation of Z A1AT polymers in liver cells predisposes carriers to cirrhosis, liver cancer and other liver pathologies.

The current treatment for the lung manifestation of AATD involves augmentation therapy using A1AT concentrates prepared from the plasma of blood donors. The US FDA has approved the use of four A1AT products: Prolastin, Zemaira, Glassia, and Aralast. Dosing is via once weekly intravenous infusion. Augmentation therapy has been demonstrated to slow progression of COPD. The liver manifestations of AATD (e.g. cirrhosis and cancer) are treated with steroids and liver transplantation. Investigational approaches to improved treatment of the liver manifestations include inhibition of Z A1AT polymerisation and increased clearance of polymers through the activation of autophagy. Investigational approaches to improved treatment of both the lung and the liver manifestations are directed towards improvement of Z A1AT folding and secretion.

Elliott et al (Protein Science, 2000, 9, 1274-1281) have described an X-ray crystal structure of A1AT and identified five cavities that are potential targets for rational drug design to develop agents that will affect Z A1AT polymerisation.

Parfrey et al (J. Biol. Chem., 2003, 278, 35, 33060-33066) have further defined a single cavity that is a potential target for rational drug design to develop agents that will affect Z A1AT polymerisation.

Knaupp et al (J. Mol. Biol., 2010, 396, 375-383) have shown that bis-ANS (4,4'-dianilino-1,1'-binaphthyl-5,5'-disulfonate) is able to bind to Z A1AT, but not to wild-type A1AT (M A1AT), with 1:1 stoichiometry and a $K_d$ of 700 nM.

Chang et al (J. Cell. Mol. Med., 2009, 13, 8B, 2304-2316) have reported a series of peptides, including Ac-TTAI-$NH_2$, that inhibit Z A1AT polymerization.

Burrows et al (Proc. Nat. Acad. Sci., 2000, 97, 4, 1796-1801) have shown that a series of non-selective chaperones, including 4-phenylbutyric acid, glycerol and trimethylamine oxide, are able to increase Z A1AT levels in cell supernatants and mouse models.

Bouchecareilh et al (Journal of Biological Chemistry, 2012, 287, 45, 38265-38278) describe the use of histone deacetylase inhibitors, in particular SAHA (suberoylanilide hydroxamic acid) to increase the secretion of both wild-type (M A1AT) and Z A1AT from cells.

Berthelier et al (PLOS ONE, May 11, 2015) have demonstrated that S-(4-nitrobenzyl)-6-thioguanosine is able to prevent Z A1AT polymerisation in vitro.

Mallya et al (J. Med. Chem., 2007, 50, 22, 5357-5363) describe a series of phenols, such as N-(4-hydroxy-3,5-dimethylphenyl)-2,5-dimethylthiophene-3-sulfonamide, able to block polymerisation of Z A1AT in vitro.

Huntington (XIIIth International Symposium on Proteinases, Inhibitors and Biological Control, 23 Sep. 2012, and 7$^{th}$ International Symposium on Serpin Biology, Structure and Function, 1 Apr. 2014) discussed a cavity from an X-ray crystal structure of Z A1AT that is a potential target for rational drug design to develop agents that will affect Z A1AT polymerisation.

U.S. Pat. No. 8,436,013B2 discloses a wide variety of structures able to increase secretion of Z A1AT from cells in the micromolar range.

WO2019/243841A1 describes compounds designed to inhibit Z A1AT polymerisation by inducing formation of a cryptic binding site within the A1AT protein structure.

WO2020/081257A1 describes compounds which are able to modulate A1AT activity, as measured using a Z A1AT elastase activity assay.

Compounds with CAS registry numbers 1797054-78-4 and 1219580-65-0 are listed in the Aurora Building Blocks catalogue.

US2007/0167621A1 describes substituted pyrimidinones including 4-{[4-[(2,4-difluorobenzyl)oxy]-2-methyl-6-oxopyrimidin-1 (6H)-yl]methyl}benzoic acid and their use in treating diseases and conditions caused or exacerbated by unregulated p38 MAP kinase and/or TNF activity.

In a first aspect of the present invention there is provided a composition comprising 4-((6-oxopyrimidin-1(6H)-yl) methyl)benzoic acid.

The compound 4-((6-oxopyrimidin-1(6H)-yl)methyl)benzoic acid is represented by formula I:

(I)

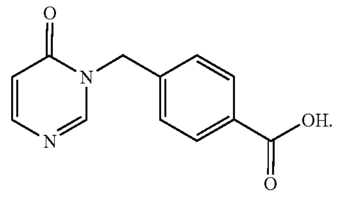 [SMILES: O=C(O)c1ccc(Cn2cnccc2=O)cc1]

The composition may be a pharmaceutical composition, for example a human pharmaceutical composition or a veterinary pharmaceutical composition.

The composition may further comprise a pharmaceutically or therapeutically acceptable excipient or carrier.

The term "pharmaceutically or therapeutically acceptable excipient or carrier" refers to a solid or liquid filler, diluent or encapsulating substance which does not interfere with the effectiveness or the biological activity of the active ingredients and which is not toxic to the host, which may be either humans or animals, to which it is administered. Depending upon the particular route of administration, a variety of pharmaceutically acceptable carriers such as those well known in the art may be used. Non-limiting examples include sugars, starches, cellulose and its derivatives, malt, gelatin, talc, calcium sulfate, vegetable oils, synthetic oils, polyols, alginic acid, phosphate buffered solutions, emulsifiers, isotonic saline, and pyrogen-free water.

All suitable modes of administration are contemplated according to the invention. For example, administration of the composition may be via oral, subcutaneous, direct intravenous, slow intravenous infusion, continuous intravenous infusion, intravenous or epidural patient controlled analgesia (PCA and PCEA), intramuscular, intrathecal, epidural, intracistemal, intraperitoneal, transdermal, topical, transmucosal, buccal, sublingual, transmucosal, inhalation, intranasal, intra-atricular, intranasal, rectal or ocular routes. The composition may be formulated in discrete dosage units and can be prepared by any of the methods well known in the art of pharmacy.

All suitable pharmaceutical dosage forms are contemplated. Administration of the composition may for example be in the form of oral solutions and suspensions, tablets, capsules, lozenges, effervescent tablets, transmucosal films, suppositories, buccal products, oral mucoretentive products, topical creams, ointments, gels, films and patches, transdermal patches, abuse deterrent and abuse resistant formulations, sterile solutions suspensions and depots for parenteral use, and the like, administered as immediate release, sustained release, delayed release, controlled release, extended release and the like.

In a further aspect of the present invention, there is provided the composition as set out above for use as a medicament.

In a further aspect of the present invention, there is provided the composition as set out above for use in treating AATD.

It has been found that 4-((6-oxopyrimidin-1(6H)-yl) methyl)benzoic acid is highly effective at increasing the levels of correctly folded and hence active Z A1AT which means that 4-((6-oxopyrimidin-1(6H)-yl)methyl)benzoic acid can be used to treat AATD.

The composition may treat AATD by inducing Z A1AT secretion.

In a further aspect of the present invention, there is provided the composition as set out above for use as an inducer of Z A1AT secretion. The use may be in vitro, for example in an in vitro assay.

In a further aspect of the present invention, there is provided the compound 4-((6-oxopyrimidin-1(6H)-yl) methyl)benzoic acid, for use as a medicament.

In a further aspect of the present invention, there is provided the compound 4-((6-oxopyrimidin-1(6H)-yl) methyl)benzoic acid for use in treating AATD.

The compound 4-((6-oxopyrimidin-1(6H)-yl)methyl)benzoic acid may treat AATD by inducing Z A1AT secretion.

In a further aspect of the present invention there is provided the compound 4-((6-oxopyrimidin-1(6H)-yl) methyl)benzoic acid for use as an inducer of Z A1AT secretion.

In a further aspect of the present invention, there is provided a use of the compound 4-((6-oxopyrimidin-1(6H)-yl)methyl)benzoic acid or the composition according to any statement set out above in the manufacture of a medicament.

In a further aspect of the present invention, there is provided a use of the compound 4-((6-oxopyrimidin-1(6H)-yl)methyl)benzoic acid or the composition according to any statement set out above in the manufacture of a medicament for treating AATD.

The compound 4-((6-oxopyrimidin-1(6H)-yl)methyl)benzoic acid or the composition according to any statement set out above may treat AATD by inducing Z A1AT secretion.

In a further aspect of the present invention there is provided a use of the compound 4-((6-oxopyrimidin-1(6H)-yl)methyl)benzoic acid or the composition according to any statement above in the manufacture of a medicament for inducing Z A1AT secretion.

In a further aspect of the present invention, there is provided a method of treating AATD, comprising administering to a subject 4-((6-oxopyrimidin-1(6H)-yl)methyl) benzoic acid or the composition according to any statement set out above.

The method may comprise the 4-((6-oxopyrimidin-1(6H)-yl)methyl)benzoic acid or the composition according to any statement above inducing Z A1AT secretion.

In a further aspect of the present invention, there is provided a method of inducing Z A1AT secretion comprising administering to a subject 4-((6-oxopyrimidin-1(6H)-yl) methyl)benzoic acid or the composition according to any statement set out above.

In a further aspect of the present invention, there is provided a use of 4-((6-oxopyrimidin-1(6H)-yl)methyl)benzoic acid or the composition according to any statement set out above as an inducer of Z A1AT secretion. The use may be in vitro, for example in an in vitro assay.

Administration of the composition as set out above or the compound 4-((6-oxopyrimidin-1(6H)-yl)methyl)benzoic acid may be via oral, subcutaneous, direct intravenous, slow intravenous infusion, continuous intravenous infusion, intravenous or epidural patient controlled analgesia (PCA and PCEA), intramuscular, intrathecal, epidural, intracisternal, intraperitoneal, transdermal, topical, transmucosal, buccal, sublingual, transmucosal, inhalation, intranasal, intra-atricular, intranasal, rectal or ocular routes.

As used herein, the term "comprising" is to be read as meaning both comprising and consisting of. Consequently, where the invention relates to a "pharmaceutical composition comprising as active ingredient" a compound, this terminology is intended to cover both compositions in which other active ingredients may be present and also compositions which consist only of one active ingredient as defined.

Unless otherwise defined, all the technical and scientific terms used here have the same meaning as that usually understood by an ordinary specialist in the field to which this invention belongs. Similarly, all the publications, patent applications, all the patents and all other references mentioned here are incorporated by way of reference in their entirety (where legally permissible).

Particular non-limiting examples of the present invention will now be described with reference to the following drawings and examples, in which:

FIG. 1 is a graph showing the dose dependent effect of 4-((6-oxopyrimidin-1(6H)-yl)methyl)benzoic acid in an in vitro Z A1AT cell secretion assay using "HEK-Z" cells (i.e. HEK-EBNA cells containing the Z A1AT plasmid). Vehicle and 10 μM SAHA were tested on each plate as controls. The x-axis shows various treatments of the cells: vehicle, SAHA and increasing concentrations of 4-((6-oxopyrimidin-1(6H)-yl)methyl)benzoic acid, the y-axis is the concentration of Z A1AT in the cell supernatant (in ng/ml).

EXAMPLES

Example 1: Preparation of 4-((6-oxopyrimidin-1(6H)-yl)methyl)benzoic acid 4-((6-oxopyrimidin-1(6H)-yl)methyl)benzoic acid was prepared using the following sequential synthesis procedures.

(a) Synthesis of tert-butyl 4-((6-oxopyrimidin-1(6H)-yl)methyl)benzoate

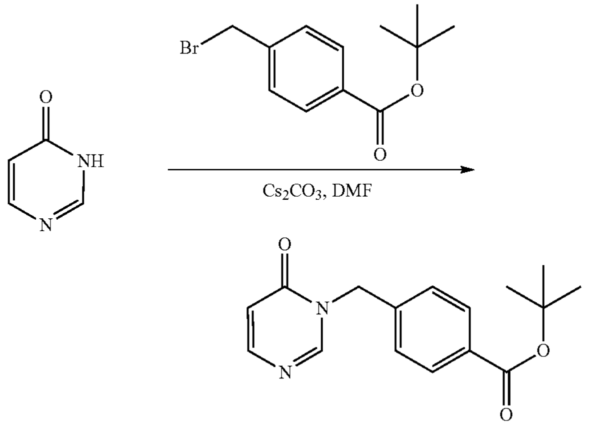

Pyrimidin-4(3H)-one (5 g, 32 mmol) and caesium carbonate (50.85 g, 156 mmol) were stirred in dimethylformamide (50 ml) for 10 minutes at room temperature. Tert-butyl 4-(bromomethyl)benzoate (14.11 g, 52 mmol) was added and the reaction was stirred for 3 hours. The reaction was diluted with water and the resulting yellow precipitate collected by filtration. The crude product was purified by column chromatography on silica, eluting with ethyl acetate/hexane (30% to 33%) to give tert-butyl 4-((6-oxopyrimidin-1(6H)-yl)methyl)benzoate. Tlc Rf 0.2 1:1 Ethyl acetate/hexane.

(b) Synthesis of 4-((6-oxopyrimidin-1(6H)-yl)methyl)benzoic acid

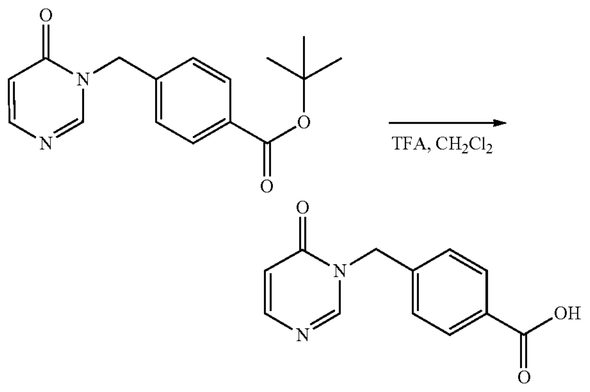

Tert-butyl 4-((6-oxopyrimidin-1(6H)-yl)methyl)benzoate (10 g, 35 mmol) was dissolved in dichloromethane (50 ml) and trifluoroacetic acid (70 ml) was added slowly. The reaction was stirred for 3 hours at room temperature. The reaction was concentrated under reduced pressure and the resulting oil stirred with diethyl ether (300 ml) for 20 minutes at room temperature. The resultant solid was collected by filtration, washed with diethyl ether (2×30 ml) and dried in vacuo to give 4-((6-oxopyrimidin-1(6H)-yl)methyl)benzoic acid.

Example 2: Activity of 4-((6-oxopyrimidin-1(6H)-yl)methyl)benzoic acid in a Z A1AT Cell Secretion Assay Using HEK-Z Cells Methods HEK-Z cells, a human embryonic kidney cell line stably transfected with the human Z AAT gene, were plated into 96 well plates ($3.0\times10^5$ cells/ml with 200 μl of media/well) overnight at 37° C. in a humidified atmosphere containing 5% $CO_2$. Following incubation cells were washed with 200 μl serum-free media three times and media was replaced with treatments in quadruplicate using vehicle, 10 μM suberanilohydroxamic acid (SAHA) or 4-((6-oxopyrimidin-1(6H)-yl)methyl)benzoic acid (at concentrations of 10, 33, 100 and 333 nM) for 48 h in a 37° C. incubator in a final volume of 200 μl. At the end of the incubation step the supernatants were removed from the wells, centrifuged at 1000×g at 4° C. for 10 min and were assayed for Z A1AT levels by ELISA (Human Serpin A1/α1-antitrypsin duo set ELISA, R&D Systems, DY1268) per manufacturer's instructions.

Briefly, a 96 well plate was coated with human A1AT capture antibody overnight at room temperature (1:180 dilution from stock, 100 μl final volume/well). The capture antibody was then removed and wells washed three times with 300 μl wash buffer (0.05% Tween 20 in PBS) and then 200 μl reagent diluent (25% Tween 20 in PBS) was incubated in each well for 1 h at room temperature. Samples, standards (125, 250, 500, 1000, 2000, 4000 and 8000 μg/ml A1AT) or blanks were then added to each well in duplicate and the plates were covered with a plate sealer and left at room temperature for 2 h. At the end of the sample incubation step, samples were removed and all wells washed as previously and 100 μl detection antibody (1:180 dilution from stock) was added to each well and incubated for a further 2 h at room temperature. Following incubation with detection antibody, supernatant was removed and wells were washed as previously and 100 μl streptavidin-HRP solution (1:200 dilution from stock) was added to each well for 20 min in the dark. After which, 50 μl stop solution (2M $H_2SO_4$) was added and optical density (OD) of each well was read at 450 nm with 570 nm blank subtracted from each well using a microplate reader. A 4 parameter logistic curve was constructed using GraphPad Prism 8 and Z A1AT concentrations were determined in each sample by interpolation from a standard curve and multiplying by the appropriate dilution factor.

Results

The amount of Z AAT secreted from HEK-Z cells into the media was measured by ELISA. SAHA at 10 μM was used a positive control.

The data in FIG. 1 show that 4-((6-oxopyrimidin-1(6H)-yl)methyl)benzoic acid secretion of Z A1AT was increased in a dose dependent manner as measured by ELISA.

The invention claimed is:

1. A method of treating $\alpha_1$-antitrypsin deficiency (AATD) in a subject in need thereof, the method comprising administering to the subject in need thereof a compound represented by the structure of

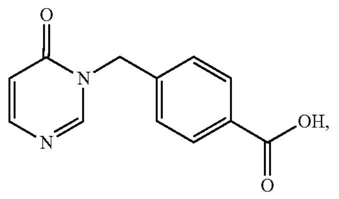 [SMILES: O=C(O)c1ccc(Cn2cnccc2=O)cc1]

or a pharmaceutically acceptable salt thereof; or a pharmaceutical composition comprising a compound represented by the structure of

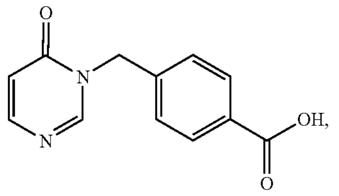

or a pharmaceutically acceptable salt thereof, and a pharmaceutically acceptable excipient.

2. The method of claim 1, wherein the administering to the subject in need thereof induces Z $\alpha_1$-Antitrypsin (A1AT) secretion in the subject.

3. The method of claim 1, wherein the administering to the subject in need thereof increases levels of Z $\alpha_1$-Antitrypsin (A1AT) in the subject.

4. The method of claim 1, wherein the administering to the subject in need thereof is conducted orally.

* * * * *